US007008591B2

(12) United States Patent
Kafesjian et al.

(10) Patent No.: US 7,008,591 B2
(45) Date of Patent: Mar. 7, 2006

(54) SUPERCRITICAL FLUID EXTRACTION PROCESS FOR TISSUE PREPARATION

(75) Inventors: Ralph Kafesjian, Newport Beach, CA (US); Myron Howanec, Jr., Corona, CA (US)

(73) Assignee: Edwards LIfesciences Corporation, Irvine, CA (US)

( * ) Notice: Subject to any disclaimer, the term of this patent is extended or adjusted under 35 U.S.C. 154(b) by 723 days.

(21) Appl. No.: 09/981,274

(22) Filed: Oct. 17, 2001

(65) Prior Publication Data

US 2003/0072677 A1    Apr. 17, 2003

(51) Int. Cl.
A16L 11/00 (2006.01)
A16F 2/76 (2006.01)
(52) U.S. Cl. .............................. 422/1; 422/28; 422/31; 435/1.1; 435/1.2; 623/915
(58) Field of Classification Search .................. 482/28, 482/31; 623/16.11, 23.72; 435/1.1, 1.2
See application file for complete search history.

(56) References Cited

U.S. PATENT DOCUMENTS

| | | | |
|---|---|---|---|
| 2,900,644 | A | 8/1959 | Rosenberg et al. |
| 3,927,422 | A | 12/1975 | Sawyer |
| 3,966,401 | A | 6/1976 | Hancock et al. |
| 3,974,526 | A | 8/1976 | Dardik et al. |
| 4,239,492 | A | 12/1980 | Holman et al. |
| 4,547,292 | A | 10/1985 | Zarchy |
| 4,553,974 | A | 11/1985 | Dewanjee |
| 4,749,522 | A | 6/1988 | Kamarei |
| 4,755,593 | A | 7/1988 | Lauren |
| 4,770,780 | A | 9/1988 | Moses |
| 4,816,159 | A | 3/1989 | Khosah et al. |
| 4,824,570 | A | 4/1989 | Bethuel et al. |
| 4,877,530 | A | 10/1989 | Moses |
| 4,880,543 | A | 11/1989 | Khosah et al. |
| 5,084,239 | A | 1/1992 | Moulton et al. |
| 5,723,012 | A | 3/1998 | Fages et al. |
| 5,725,579 | A | 3/1998 | Fages et al. |
| 5,877,005 | A | 3/1999 | Castor et al. |
| 6,214,054 | B1 | 4/2001 | Cunanan et al. |
| 6,217,614 | B1 * | 4/2001 | Fages et al. ............. 623/16.11 |
| 6,613,278 | B1 * | 9/2003 | Mills et al. .................... 422/33 |
| 6,652,818 | B1 * | 11/2003 | Mills et al. .................. 422/295 |
| 2001/0003007 | A1 | 6/2001 | Chinn et al. |

FOREIGN PATENT DOCUMENTS

| WO | WO 85/04816 A1 | 11/1985 |
|---|---|---|
| WO | WO 94/03590 | 2/1994 |
| WO | WO 02/07785 A2 | 1/2002 |

OTHER PUBLICATIONS

Fages, et al., "Supercritical Fluid Extraction: A New Way of Manufacturing Biomaterials," 21st Annual Meeting of the Society for Biomaterials, Mar. 18-22, 1995, San Francisco, California, p. 236.
Fages, et al., "Use of supercritical CO2 for Bone Delipidation," Biomaterials 1994, vol. 15, No. 9., pp 650-656.
Fages, et al., "Use of Supercritical Fluid Extraction as a Method of Cleaning Anterior Cruciate Ligament Prostheses In Vitro and In Vivo Validation," ASAIO Journal 1998, pp. 278-288.
McCoy, Michael "Industry Intrigued by CO2 as Solvent," C&EN Northeast News Bureau, pp. 11-13, Jun. 14, 1999 C&EN.
Mishra, et al., "Extraction and Purification of w-3 Fatty Acids With an Emphasis on Supercritical Fluid Extraction-A Review," Food Research International 26(3) (1993) 217-226.
Chester, et al., "Supercritical Fluid Chromatography and Extraction," Analytical Chemistry, vol. 68. No. 12, Jun. 15, 1996, pp. 487-514.
Gueclue-Uestuendag, et al. "Correlating the Solubility Behavior of Fatty Acids, Mono-, Di-, and Triglycerides, and Fatty Acid Esters in Supercritical Carbon Dioxide," Ind. Eng. Chem. Res. 2000, 39(12), 4756-4766.
Fages, et al., "Use of Supercritical CO2 for Bone Delipidation," Biomaterials 15(9):650-6, 1994 Jul—Abstract.
Fages, et al., "Use of Supercritical Fluid Extraction as a Method of Cleaning Anterior Cruciate Ligament Prostheses: in Vitro and in Vivo Validation," ASAIO Journal, 44(4):278-88, Jul.-Aug. 1998—Abstract.
Fages, et al., "Viral inactivation of Human Bone Tissue Using Supercritical Fluid Extraction," ASAIO Journal. 44 (4):289-93, Jul.-Aug. 1998 —Abstract.
Ishikawa, et al., "Sterilization of Microorganisms by the Supercritical Carbon Dioxide Micro-Bubble Method," Bioscience, Biotechnology & Biochemistry. 59(10):1949-50, Oct. 1995—Abstract.
van Bavel et al., et al., "Supercritical Fluid Extraction of PCBs from Human Adipose Tissue for HRGC/LRMS analysis," Chemosphere.30(7):1229-36, Apr. 1995—Abstract.
Frayssinet, P., et al., "Histological Integration of Allogenic Cancellous Bone Tissue Treated by Supercritical CO2 Implanted in Seep Bones," Biomaterials. 19(24):2247-53, Dec, 1998—Abstract.
Koshevoi, et al., "Diffusion Coefficients of Triglycerides and Fatty Acids in Supercritical Carbon Dioxide," Pishch. Tekhnol. (2000), (2-3), 62-63—Abstract.
Kim, et al., "Supercritical Fluid Extraction of Unsaturated Fatty Acids from Soybean Oil," Hwahak Konghak (1992), 30(6), 635-40—Abstract.

* cited by examiner

Primary Examiner—Krisanne Jastrzab
(74) Attorney, Agent, or Firm—Rajiv Yadav

(57) ABSTRACT

The present invention provides methods for preparing tissue for incorporation into xenografts and bioprosthetic devices. The methods of the invention make use of supercritical fluids to remove infectious materials and chemical agents from tissues, as well as to permeate a tissue with a chemical agent (e.g. tanning, cross-linking, and bioactive agents).

36 Claims, No Drawings

SUPERCRITICAL FLUID EXTRACTION PROCESS FOR TISSUE PREPARATION

BACKGROUND OF THE INVENTION

Implantable xenografts and prosthetic devices are typically sterilized prior to implantation in an intended recipient. Sterilization is required to ensure that the devices do not introduce potential pathogens, or other biologically detrimental agents into the intended recipient. Sterilization is particularly relevant where biomaterials from human or other mammalian donors are constituents of the graft or device. For example, U.S. Pat. No. 6,214,054 to Cunnanen et. al (incorporated herein in its entirety) includes discussion of well recognized sterilization techniques for such biological tissues. Device components are sterilized individually prior to assembling the device or, alternatively, they are sterilized by the process of "terminal sterilization". In the terminal sterilization process, the device is sterilized following its construction, i.e., after all the components have been combined with one another in the device. Both processes may be used in combination to ensure complete sterilization of the graft or device. A variety of physical or chemical methods have been developed for use in sterilization and include, for example, exposure to chemicals or heat, or exposure to ionizing or non-ionizing radiation. These methods, however, have inherent problems. Moreover, most of the methods are inappropriate for bioprosthetic devices incorporating mammalian tissue.

Exemplary sterilization methods include treating prosthesis and graft components with chemical reagents. The chemical reagents themselves, or reaction byproducts derived from the reagents, can be harmful to the intended recipient of the prosthetic device. Accordingly, such chemicals must be removed prior to implantation of the devices. Common chemical sterilizing agents include ethylene oxide and formaldehyde, both of which are alkylating agents and, therefore, can modify and inactivate biologically active molecules. Both of these chemicals are, however, known to be carcinogens and mutagens (Davis et al., (1973) "Microbiology, 2nd Ed.", Harper and Row, Publishers).

Other methods of sterilizing device components include exposing the device or components thereof to plasma (Moulton et al., U.S. Pat. No. 5,084,239) heat, or ionizing radiation. Similar to chemical treatment, however, where the device includes biological components (e.g. proteins, cells, tissues), exposing the device to elevated temperatures, radiation or plasma is not desirable because proteins and other biological materials can be denatured and subsequently inactivated or weakened by exposure to these forms of energy. Although the sterilization of objects by exposure to ionizing and non-ionizing radiation obviates the necessity of adding potentially toxic chemicals, the radiation energy and/or its byproducts, including oxygen free radicals, are competent to modify protein conformation and so can damage or destroy proteins, cells and tissue. In addition, exposure of some medically important polymers, for example, polyurethane or polymethylmethacrylate to gamma radiation can result in immediate and long term physical changes to the polymer. Moreover, irradiation with gamma or beta rays does not destroy all pathogens with certainty. Indeed, certain viruses are radiation resistant. Thus, alternatives to sterilizing xenografts and biologically derived components of prosthetic devices with chemicals and radiation are being avidly sought.

The chemical- and radiation-based methods for sterilizing biologically derived prosthetic device components described above, rely on the inactivation of infectious agents associated with the biological component of the device. The inactivated infectious agent generally remains associated with the biological component of the device. A promising mode of rendering a biologically derived material non-infectious relies on inactivating infectious agents by contacting them with supercritical fluids. Little attention, however, has been focused on the use of supercritical fluids to extract infectious materials from mammalian soft-tissue.

Supercritical fluids have principally been used in the field of chromatography, where these dense materials are employed as extraction solvents and interactive mobile phases. For example, U.S. Pat. Nos. 4,816,159 and 4,880,543 to Khosah et al., each disclosing supercritical fluid chromatography methods that utilize specific packing materials. The packing materials disclosed in these patents are selected from metal oxide/hydroxide support materials having phosphorous-containing organic molecules bonded to reactive sites on the support materials. Historically, supercritical fluid chromatography has its origins in the mid-1960s, while its extraction analogue has only recently seen application in the field of analytical chemistry.

Extraction methods utilizing supercritical fluids have also been utilized for a number of applications. Distinct from chromatography using supercritical fluids, supercritical fluid extraction is a technique whereby organic compounds can be extracted from sample matrices utilizing a dense gas-like material, such as supercritical carbon dioxide. The solvation power of carbon dioxide is increased as the pressure and temperature are increased above their critical points, which are 1070 psi and 31° C., respectively. For example, U.S. Pat. No. 4,547,292 to Zarchy; U.S. Pat. No. 4,770,780 to Moses; U.S. Pat. No. 4,824,570 to Bethuel et al; U.S. Pat. No. 4,877,530 to Moses; and International Patent No. WO 85/04816 each disclose various processes or systems useful for practicing extraction utilizing supercritical fluids. Other references discussing supercritical fluid extraction include, Favati et al., *J. Food Science* 53: 1532–1536 (1988); King *J. Chromatographic Science* 27: 355–364 (1989); and King et al. *J. Agricultural & Food Chemistry* 37: 951–954 (1989).

A number of references disclose the use of supercritical fluids to inactivate microbes and viruses. For example, the mechanical destruction of microbial cells by sudden decompression in carbon dioxide $CO_2$ in the supercritical state has been described (Nakamura et al., *Biosci. Biotech. Biochem.* 58(7): 1297–1301 (1994)). Castor et al. (U.S. Pat. No. 5,877,005) disclose a method for inactivating a virion in a fluid containing a biological material. Bone grafts have been prepared by extracting lipid materials from the solid framework of the graft using supercritical fluid extraction. For example, EP-A-0.603.920 describes a process for the treatment of bone tissues in which a fluid in the supercritical state is used to extract lipidic organic matter. Supercritical fluid extraction has been used to remove both lipidic material and viruses from bone material. Representative references disclosing the removal of viruses from bone include, Fages et al., 21st Annual Meeting of the Society for Biomaterials, San Francisco, Calif., p. 238 (1995); Fages et al., Biomaterials 15: 650–656 (1994); Fages, U.S. Pat. Nos. 5,723,012; and 5,725,579.

The references set forth above disclose processes for inactivating infectious agents in bone and cartilage using supercritical fluids. The references disclose that to obtain implantable tissue, the bone graft material must be subjected to a number of steps in addition to the supercritical fluid extraction, including chemical treatment (with hydrogen peroxide) and/or enzyme treatment (protease) for extracting residual proteins. The tissue is then washed, dehydrated and disinfected in baths of ethanol (this last stage increasing safety as regards infection of the biomaterial). None of the references suggests that infectious materials can be effectively removed from soft-tissue by supercritical fluid extraction. Moreover, none of the references suggests that treatment of any tissue with supercritical fluids alone will remove infectious agents from the tissue.

Of increasing concern is the presence of infectious prions in biologically derived materials used for xeonografts and prosthetic devices. The widespread occurrence of prion-related disease and the possibility of interspecies transmission has serious implications for the biotechnology industry, which derives many of its products from mammalian tissue (Di Martino *Biologicals* 21 : 61–66 (1993)). Concerns about the safety of mammalian tissue products has led to studies on the inactivation of prions. These studies indicate that prions are more resistant toward inactivation than more conventional pathogens such as viruses or bacteria. Thus, relatively harsh conditions are required to decontaminate prion-containing biological materials. The only methods currently known to disinfect prion contaminated biological preparations are prolonged autoclaving at 130° C. or above, and treatment with concentrated sodium hydroxide solution. These methods have been recommended for routine inactivation of prions (Department of Health and Social Security Circular 84: 16 (1989)). It has also been reported that 100 kD cutoff ultrafiltration in combination with treatment with 6M urea results in decontamination of prion containing preparations (Pocchiari et al., *Arch. Virol.* 98: 131–135 (1988)). Other methods capable of lowering prion activity include treatment with organic solvents, detergents, protein-denaturing agents, chaotropic salts and phenol (Millson et al., in Prusiner and Hadlow, eds. SLOW TRANSMISSIBLE DISEASES OF THE NERVOUS SYSTEM, vol. II. New York: Academic Press 409–424 (1979); Prusiner et al., *PNAS* 78: 4606–4610 (1981); Kimberlin et al., *J. Neurol. Sci.* 59: 390–392 (1983); Walker et al., *Am. J. Public Health* 73: 661–665 (1983); Brown et al.,*J. Infect. Dis.* 153: 1145–1148 (1986)).

The extreme conditions required to eliminate infectivity, and particularly prion infectivity, in biomaterials are typically incompatible with methods intended to preserve the useful activity and structure of these materials. The harsh conditions of prior methods are particularly deleterious to mammalian soft-tissue, resulting in the denaturation of functional and structural components of the tissues. There is, thus, a need for a method for removing infectious materials from mammalian soft-tissues that does not compromise the integrity of these desirable biomaterials.

SUMMARY OF THE INVENTION

It has now been discovered that supercritical fluid extraction of mammalian soft-tissue derived biomaterials removes infectious materials, including prions, rendering the biomaterials safe and effective for use as xenografts and as components of bioprosthetic devices. Supercritical fluids have also been discovered to be excellent vehicles for delivering chemical agents to tissue of use in xenografts and prosthetic devices. Moreover, it has been discovered that supercritical fluid extraction can be used following more conventional chemical treatment to remove residual chemical agent from the tissue. The methods of the present invention are effective at low temperatures and under conditions that are notably more mild than those of art-recognized methods for removing infectious agents from tissues.

Fluids in the supercritical state have been shown to extract organic matter, particularly lipidic matter, from bone tissue. Little attention has been paid, however, to the use of supercritical fluids in preparing mammalian soft-tissues for use in bioprosthetic devices. Among the uses of supercritical fluids in preparing soft-tissue are removing infectious agents and chemical agents from the tissue. Supercritical fluids are also useful as solvents for delivering and removing chemical agents (e.g., tanning agents, cross-linking agents, bioactive agents, etc.), which are used to treat soft tissue xenografts and components of bioprosthetic devices.

Thus, in a first aspect, the present invention provides a method of removing or inactivating infectious agents from mammalian soft-tissue. The method includes subjecting the soft-tissue to extraction with a medium comprising a supercritical fluid, thereby removing or inactivating the infectious agents. Similarly, the invention can be tailored to extract undesirable compounds form the tissue, for example, compounds that accelerate or produce calcification of pericardial heart valve tissue.

The process of the invention can also be used to saturate a porous tissue matrix with a chemical agent, such as a cross-linking agent for stabilizing the tissue prior to its use as a xenograft or as a component of a bioprosthetic device. Due to the uniquely penetrating quality of supercritical fluids, these fluids and solutes dissolved in them penetrate more rapidly, deeply and completely into a tissue structure than simple solutions of a chemical agent. Thus, using the methods of the present invention, it is possible to more thoroughly permeate a tissue with a chemical agent in a shorter period of time under milder conditions than is possible using non-supercritical solutions chemical agents.

Thus, in a second aspect, the present invention provides a method of treating a mammalian tissue with a chemical agent. The method includes contacting the tissue with the chemical agent dissolved in a supercritical fluid.

In addition, the invention provides a method for removing excess chemical agents, e.g., fixing agents, cross-linking agents, preservatives and the like, from a tissue following its treatment with one or more chemical agent.

Thus, in a third aspect, the invention provides a method for removing a chemical agent from a tissue following the treatment of the tissue with the chemical agent. The method includes contacting the tissue with a supercritical fluid under conditions that remove the chemical agent from the tissue.

Other objects and advantages of the methods of the present invention will be apparent from the detailed description that follows.

DETAILED DESCRIPTION OF THE INVENTION AND THE PREFERRED EMBODIMENTS

Definitions

As used herein, the term "contacting" means exposing to and coming together.

As used herein, "chemical agent," refers to agents used to prepare tissues for incorporation into xenografts and bioprosthetic devices. Exemplary chemical agents include, but are not limited to, tanning agents, fixatives, cross-linking agents, alkylating agents, and acylating agents. Example of useful bioactive chemical agents include, but are not limited to, antithrombotics, antiinflammatories, corticosteroids, agents affecting microtubule polymerization, structure and function, agents that affect platelet activation and aggregation, and degradation, antisense oligonucleotides, antineoplastics, antioxidants, agents affecting reactive oxygen, calcium channel blockers, converting enzyme inhibitors, cytokine inhibitors, growth factors, growth factor inhibitors, growth factor sequestering agents, immunosuppressives, antimicrobial agents, antiviral agents, antifungal agents, immunosuppressive agents, tissue factor inhibitor, smooth muscle inhibitors, organoselenium compounds, retinoic acid, retinoid compounds, sulfated proteoglycans, polyanions, immunosuppressants, superoxide dismutase mimics, NO, NO precursors and combinations thereof.

Certain biologically active chemical agents falling within the above-recited classes are presently preferred. For example, when one or more of the bioactive agents is an antithrombotic agent, it is preferably selected from heparin, hirudin or a combination thereof. When one or more of the bioactive agents is a corticosteriod, it is preferably selected from dexamethasone, a dexamethasone derivative or a combination thereof. When one or more of the bioactive agents is an antimicrotubule agent, it is preferably selected from taxane, a derivative of taxane or a combination thereof. When one or more of the bioactive agents is an antiplatelet agent, the agent is preferably an inhibitor of collagen synthesis, such as halofuginore, derivatives of halofuginore, proteins (e.g., $GpII_bIII_a$, ReoPro™) or a combination thereof.

Pharmaceutically acceptable salts of the biologically active chemical agents are also of use in the present invention. Exemplary salts include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, trifluoroacetic and the like.

Other agents that are useful in conjunction with the present invention will be readily apparent to those of skill in the art.

The term, "sterilization" as used herein, refers to an act or process using either physical or chemical means for eliminating or inactivating substantially all viable organisms, especially micro-organisms, viruses and other pathogens, associated with a xenograft or bioprosthetic device. As used herein, "sterilized" includes devices achieving a sterility assurance level of $10^{-6}$, as determined by FDA (Federal Drug Administration) standards.

The term, "terminal sterilization" as used herein, refers to the last step in the fabrication of a device wherein the device is sterilized after its assembly.

The term "ionizing radiation" as used herein, refers to particles or photons that have sufficient energy to produce ionization directly in their passage through a substance, e.g., the therapeutic device contemplated herein.

In industrial settings where critical, supercritical and near critical fluids are used, it is common, particularly where the solvent properties are being applied, to use the term "critical" to refer to supercritical, critical and near critical fluids. This present invention uses the term "supercritical" to represent supercritical, critical or near critical fluids.

Supercritical fluids exhibit solvent powers related to the solvent density at a particular temperature and pressure. Solvating properties of supercritical fluids are influenced by cosolvents and entrainers. The terms "cosolvents" and "entrainers" are used interchangeably to suggest compositions, which are soluble in the supercritical fluid and impart desirable solubility features to the supercritical fluid to which they are added.

Introduction

The present invention is directed to the use of supercritical fluids in preparing mammalian tissue for incorporation into xenografts and bioprosthetic devices. Supercritical fluids are used to remove or inactivate infectious agents from the tissue under mild conditions, which do not significantly degrade or denature tissue proteins. Supercritical fluids are also used to deliver chemical agents to tissues and to remove excess chemical reagents therefrom.

Fluids in the supercritical state are materials, which are under conditions of temperature and pressure such that their properties are intermediate between those of gases and those of liquids. They are also called "dense gases" or "expanded liquids". For a given chemical substance, the precise point on the temperature-pressure diagram at which the two phases, liquid and vapor form only one phase is called the critical point. Beyond this critical temperature ($T_c$) and critical pressure ($P_c$), the fluid is in the so-called "supercritical" state.

Supercritical Fluids

In the field of physical chemistry, the term "critical fluid" refers to a gas at or above its critical temperature and at or above its critical pressure. The term "supercritical fluid" refers to a gas above its critical temperature and above its critical pressure. Supercritical fluids are sometimes designated in this application by the abbreviation "SCF." The term "near critical" is used in the sense of approaching or close to being critical. At or near the critical pressure and temperature supercritical fluids conform to the equation:

$$T_r = T_o/T_c$$

where $T_r$ is the reduced temperature in absolute degrees; $T_o$ is the absolute operating temperature; and $T_c$ is the absolute critical temperature. A preferred range of $T_r$ is 0.1 to 2.0.

At or near the critical pressure and temperature supercritical fluids conform to the equation:

$$P_r = P_o/P_c$$

where $P_r$ is the reduced pressure; $P_o$ is the operating pressure; and $P_c$ is the critical pressure. A preferred $P_r$ is 0.2 to 20.0, and most preferably 0.5 to 10.0. As used herein, the term "near critical" means having a reduced pressure, $P_r$ of 0.2–1.0 and/or reduced temperature, $T_r$, of 10–1.0.

One example, without limitation, of a near critical fluid is a gas having a temperature below its critical temperature and a pressure at or above the critical pressure. Such gas has properties, which may approach those of a supercritical or critical fluid, particularly in solvating properties.

Supercritical fluids of use in practicing the processes of the present invention include any supercritical fluid, either substantially pure or containing additives, such as cosolvents (e.g., ethanol, methanol, acetone, and ethylene glycol). Cosolvents can be introduced to affect, inter alia, the polarity of the critical fluid, thereby enhancing the capacity of the critical fluid to extract or deliver certain materials. Other useful additives are those that act to entrain or solvate species, such as infectious agents and chemical agents, thereby facilitating the removal of these agents from the tissue (e.g., surfactants, detergents, cyclodextrin, etc.).

Other supercritical fluids of use in the present invention are those in which chemical agents such as fixatives, tanning agents, preservatives, bioactive chemical agents and the like are soluble. Although any supercritical fluid that has desirable characteristics for a particular application can be used to practice the present invention, certain supercritical fluids are presently preferred.

Preferred fluids are those that are gases at ambient conditions and that have critical temperatures of between 0° C. and 100° C., most preferably between 0° C. and 60° C. When working with soft-tissue, fluids with critical temperatures of less than 60° C. are preferred so as to further preserve the structural integrity and biological activity of the soft-tissue. As a practical matter, a temperature of above 0° C. is desired with aqueous systems to avoid freezing the sample.

Preferred supercritical fluids are selected based upon at least two factors. The fluid selected is capable of permeating the tissue and extracting from or delivering to the tissue a desired agent. Secondly, the fluid should is selected to minimize the effect on the material being treated. Presently preferred supercritical fluids include, for example, one or more compounds of the group consisting of fluorocarbons, alkanes and mixtures thereof. Preferred fluorocarbons include, but are not limited to, chlorodifluoromethane and trifluoromethane. Preferred alkanes include one or more compounds of the group consisting of ethylene, propane and ethane. Still further preferred supercritical fluids are nitrous oxide, nitrogen and carbon dioxide.

In the discussion that follows, the present invention is illustrated by examples using carbon dioxide in the supercritical state to treat mammalian soft-tissue. The focus on the use of supercritical carbon dioxide is for clarity of illustration and should not be construed as defining or limiting the scope of the invention.

Extraction of Infectious Agents Using Supercritical Fluids

In a first aspect, the present invention provides a method of removing infectious agents from mammalian soft-tissue. The method includes subjecting the soft-tissue to extraction with a medium comprising a supercritical fluid, thereby removing the infectious agents from the tissue.

Exemplary infectious agents removed from the tissue using the process of the invention include, viruses, bacteria, mycobacteria, mycoplasma, fungi, prions and constituents thereof. The invention is applicable to combating viruses of the family of Togaviridae, in particular of the genus Alphavirus, such as the Hepatitis C virus, and for preventing their transmission during tissue grafts; for combating viruses of the family Picorviridae, in particular of the genus Enterovirus, more particularly the Polio Sabin virus, and preventing their transmission during tissue grafts; for combating viruses of the family Herpesviridae and preventing their transmission during tissue grafts; for combating viruses of the family Retroviridae, in particular of the genus Lentivirus, more particularly human HIV immunodeficiency viruses, and preventing their transmission during tissue grafts. Of particular interest is the use of the methods of the present invention to remove prions for a tissue.

The tissues with which the present method is practiced include substantially any mammalian soft-tissue that is useful in preparing a prosthetic device having a biological component thereto. For example, in one embodiment, the tissue is derived from an organ. In another embodiment, the soft-tissue is selected from nerve tissue, glandular tissue (e.g., lymphatic tissue), respiratory tissue, digestive tissue, urinary tract tissue, sensory tissue (e.g., cornea, lens, etc.), and reproductive tissue.

In presently preferred embodiments, the tissue is selected from muscle tissue, adipose tissue, epithelial tissue and endothelial tissue. In particularly preferred embodiments, the tissue is selected from myocardial tissue and vascular tissue.

The supercritical fluids of use in practicing this aspect of the present invention include pure supercritical fluids and mixtures of supercritical fluids with diluents, surfactants, detergents, organic solvents (e.g. alcohols, ketones, esters, DMSO, DMF, hydrocarbons, etc.), entrainers (e.g., cyclodextrin, charged polysaccharides, and molecules that specifically bind to infectious agents or sites on a tissue that recognize and interact with an infectious agent. For example, it is within the scope of the present invention to include within a supercritical fluid a molecule that competes with an infectious agent for a binding site for the infectious agent on a tissue.

In a presently preferred embodiment, the supercritical fluid includes an alcohol selected from ethanol, n-propanol and combinations thereof. In other preferred embodiments, the supercritical fluid contains acetone, sodium hydroxide, ethylene glycol, polyethylene glycol, polyethylene oxide or other PEG or PEO related compounds.

The determination of the correct amount of supercritical fluid and the identity and amount of any cosolvent or entrainer needed for a particular application is well within the abilities of those of skill in the art. For example, a tissue is extracted one or more times with a supercritical fluid and the extracted material is collected. The amount of infectious material or chemical agent removed by the extraction is determined. When the supercritical fluid ceases to remove infectious agent and/or chemical agent from the tissue an end point is reached, which is indicative of the amount of supercritical fluid necessary to remove the particular agent from the tissue.

In an exemplary embodiment, the methods of the present invention use supercritical carbon dioxide. The tissue is treated with substantially any amount of supercritical carbon dioxide that provides the sought after results. The critical temperature of carbon dioxide, 31° C., is low. Thus, carbon dioxide can be in the supercritical state while working at a temperature of around 31° C. and a pressure of around 7.38 MPa. According to the pressure applied, it is convenient to work at temperatures between about 31° C. and about 60° C., at which temperatures the denaturing of constituents of the tissue is minimized. Moreover, the solvent power of carbon dioxide is excellent. For example, it is known that many fatty acids and triglycerides have solubility in carbon dioxide in the supercritical state of up to 10%.

In a preferred embodiment utilizing carbon dioxide, the tissue is treated with about 100 to about 500 grams of supercritical carbon dioxide/gram of tissue. The extraction can be performed as a single step. Alternatively, the extraction can be performed as a series of sequential steps. At the end of each sequential step, the carbon dioxide containing the extracted agent is preferably removed from the tissue prior to contacting the tissue with a new fraction of carbon dioxide.

In another preferred embodiment, the tissue is treated with a flow of supercritical fluid. In this embodiment, the tissue is preferably treated with carbon dioxide for a period determined as a function of carbon dioxide flow rate in order to permit passage of about 100 grams to about 500 grams of supercritical carbon dioxide/gram of tissue. More preferably, the tissue is treated with carbon dioxide for a period determined as a function of carbon dioxide flow rate in order to permit passage of about 200 grams to about 400 grams of supercritical carbon dioxide/gram of tissue.

The method of the invention is practiced with supercritical fluids at any practicable pressure. The extraction pressure is selected such that the fluid is maintained in its supercritical state. In a presently preferred embodiment using supercritical carbon dioxide, the carbon dioxide is applied to the tissue at a pressure between about $1 \times 10^7$ Pa and about $5 \times 10^7$ Pa. In another preferred embodiment, the supercritical carbon dioxide is applied at a pressure between about $2 \times 10^7$ Pa and $4 \times 10^7$ Pa.

The temperature of the supercritical fluid is preferably maintained low enough to minimize thermal damage to the tissue while allowing the supercritical fluid to efficiently extract the contaminating agent from the tissue. In a preferred embodiment, using supercritical carbon dioxide the supercritical fluid is applied at a temperature between about 30° C. and about 60° C., more preferably from about 40° C. to about 50° C.

At the completion of the extraction or delivery process, the tissue is preferably separated from the critical fluid under aseptic conditions. In a preferred embodiment, to accomplish separation, the mixture is decompressed thereby resulting in a phase separation of the fluid from the tissue. The tissue then is isolated under aseptic conditions.

Supercritical Fluids Delivering Tissue Additives

In a second aspect, the present invention provides a method of treating a tissue with a chemical agent. The method includes contacting the tissue with the chemical agent dissolved in a supercritical fluid. The general and preferred characteristics of the supercritical fluids discussed in the sections above are equally applicable to the present aspect of the invention.

The fluid in the supercritical state, i.e. one having low dynamic viscosity (close to that of a gas), a high diffusion coefficient, very low interfacial surface tension and high density (close to that of a liquid) diffuses easily through the tissue without any absorptivity problem. In addition, the solvent power of such a fluid is high (close to that of liquids and sometimes up to $10^8$ times that of a gas), and may be modified by varying the pressure. The result of this is that such a fluid in the supercritical easily dissolves the chemical agent state and penetrates the tissue thoroughly to efficiently deliver the chemical agent thereto.

Supercritical fluids are highly penetrating delivery vehicles for chemical agents that modify tissue properties. Exemplary tissue properties modified by delivery of a chemical agent in a supercritical fluid include, immunogenicity, strength, water content, durability and resistance to infection, thrombogenesis, rejection and degradation in vivo and in vitro. The chemical agents delivered by the supercritical fluid are also useful to modify surface characteristics (e.g., hydrophobicity, hydrophilicity, charge, polarity, etc.) of the tissue. Exemplary chemical agents delivered to a tissue using a supercritical fluid as a delivery agents include, but are not limited to, tissue fixatives, cross-linking agents, preservatives, drugs (e.g. antibacterials, antivirals, antifungals, immunosuppressants, and the like).

In an exemplary embodiment, a supercritical fluid delivers a chemical "tanning agent." Xenograft materials are typically chemically "tanned" or "cross-linked" to reduce immunogenicity prior to implantation into a recipient. For example, glutaraldehyde is used to cross-link or "tan" xenograft tissue in order to reduce its antigenicity, as described in Brig detail in Lauren (U.S. Pat. No. 4,755,593). Various chemical tanning or "fixing" procedures have been used to preserve and prevent the breakdown of collagenous tissue grafts. Such "fixing" procedures generally involve the bathing or immersion of the collagenous graft tissue in a collagen cross-linking reagent. Examples of methods for preparing chemically cross-linked collagen or graft materials are found in Rosenberg et al. (U.S. Pat. No. 2,900,644), Sawyer (U.S. Pat. No. 3,927,422), Hancock et al. (U.S. Pat. No. 3,966,401), Dardik et al. (U.S. Pat. No. 3,974,526), Holmun et al (U.S. Pat. No. 4,239,492) and Dewanjee (U.S. Pat. No. 4,553,974). Amongst the substances most widely used for fixing biological materials are aldehydes. In particular, glutaraldehyde, formaldehyde, the glyoxals and other aldehydes are used. These compounds can create networks of bonds, which stabilize the tissue. Glutaraldehyde and formaldehyde, in particular, are known for their stabilizing effect.

Other agents such as aliphatic and aromatic diamine compounds provide additional cross-linking through the side-chain carboxyl groups of aspartic and glutamic acid residues of tissue polypeptides. Glutaraldehyde and diamine tanning also increases the stability of the tissue. Diamine tanning may be performed before, along with, or following fixing with an aldehyde, for example. Both aliphatic and aromatic diamines may be used. Mixtures of structurally different diamines and aldehydes are useful in providing a range of chain lengths, which increases the probability of bond formation.

Additional agents and methods of tanning and fixing tissues, and the identity and amount of a particular agent delivered to a tissue, for a particular application, are parameters whose selection is well within the ability of those of skill in the art. To the extent that a method for preparing a tissue utilizes a supercritical fluid to deliver a chemical agent to a tissue, the methods are within the scope of the present invention.

In an exemplary embodiment, the tissue is treated with glutaraldehyde, which is dissolved in a supercritical fluid, which is preferably carbon dioxide. The amount of glutaraldehyde taken up by the tissue can be measured by art-recognized methods, such as determining the decrease in the amount of glutaraldehyde in the supercritical delivery vehicle. Methods of determining aldehyde presence and concentration, and differentiating aldehydes from other organic compounds are well known in the art. In an exemplary embodiment, tissue fixation is terminated when a predetermined amount of glutaraldehyde is taken up by the tissue, or when the tissue ceases to uptake glutaraldehyde.

Supercritical Fluids to Extract Excess Chemical Agent

In a third aspect, the present invention provides a method of removing excess chemical agents from a tissue by extracting the tissue with a supercritical fluid. According to the invention, the fluid in the supercritical state penetrates the tissue at a stage in its processing in which the chemical agent is present in the tissue. The chemical agent is solubilized in the fluid in the supercritical state, and is thereby extracted from the tissue. The general and preferred characteristics of the supercritical fluids discussed in the sections above are equally applicable to the present aspect of the invention.

Treatment of tissues with chemical agents, e.g., aldehydes, can give rise to diverse effects such as cytotoxicity, the inducing of mineralization, the development of inflammatory reactions, etc. In fact, many authors have described the presence of aldehyde residues as one of the main contributory causes of tissue calcification which, for example, in biological heart-valve prostheses, causes many of the complications attributable to the prosthesis. Additionally, it has been found that lipids initially present in the tissue may contribute to calcification.

The pairing of chemical agent with supercritical extraction solvent is within the ability of those of skill in the art. In an exemplary embodiment, the solubility of the agent in the supercritical fluid is first determined in the absence of the tissue. When a supercritical fluid in which the agent is soluble is identified, the tissue is extracted with the supercritical fluid. Alternatively, a mixture of supercritical fluids can be tailored to improve extraction of a chosen class of compounds. The efficiency or end point of an extraction is determined by, for example, collecting a predetermined amount of supercritical extraction effluent, which is subsequently analyzed for its content of the chemical agent removed from the tissue.

Alternatively, in another exemplary embodiment, it is desired to allow a predetermined amount of the chemical agent in the tissue (e.g. drugs or other bioactive agents). In this embodiment, the tissue loaded with the agent and a predetermined amount of excess agent is removed from the tissue by supercritical fluid extraction.

As with the aspect of the invention in which infectious materials are removed from a tissue or a chemical agent is delivered to a tissue, it is within the scope of the present invention to include cosolvents and entrainers within the supercritical fluid to facilitate the extraction of the chemical agent from the tissue.

It is understood that the examples and embodiments described herein are for illustrative purposes only and that various modifications or changes in light thereof will be suggested to persons skilled in the art and are to included within the spirit and purview of this application and are considered within the scope of the appended claims. All publications, patents, and patent applications cited herein are hereby incorporated by reference in their entirety for all purposes.

What is claimed is:

1. A method of removing prions from mammalian soft-tissue, said method comprising subjecting said soft-tissue to extraction with a medium comprising a supercritical fluid, thereby removing said prions.

2. The method according to claim 1, wherein said prions are causative agents of spongiform encephelopathy.

3. The method according to claim 1, wherein said fluid is carbon dioxide.

4. The method according to claim 3, wherein the tissue is treated with about 100 to about 500 grams of supercritical carbon dioxide/gram of tissue.

5. The method as claimed in claim 4, wherein the tissue is treated with carbon dioxide for a period determined as a function of carbon dioxide flow rate in order to permit passage of about 100 grams to about 500 grams of supercritical carbon dioxide/gram of tissue.

6. The method according to claim 5, wherein the tissue is treated with carbon dioxide for a period determined as a function of carbon dioxide flow rate in order to permit passage of about 200 grams to about 400 grams of supercritical carbon dioxide/gram of tissue.

7. The method according to claim 4, wherein the supercritical carbon dioxide is applied at a pressure between about $1 \times 10^7$ Pa and about $5 \times 10^7$ Pa.

8. The method according to claim 7, wherein the supercritical carbon dioxide is applied at a pressure between about $2 \times 10^7$ Pa and $4 \times 10^7$ Pa.

9. The method according to claim 4, wherein the supercritical carbon dioxide is applied at a temperature between about 40° C. and about 55° C.

10. The method of claim 1, wherein said supercritical fluid is selected from one or more compounds of the group consisting of fluorocarbons, and alkanes.

11. The method of claim 10, wherein said fluorocarbons are selected from one or more compounds of the group consisting of chlorodifluoromethane and trifluoromethane.

12. The method of claim 10, wherein said alkanes are selected from one or more compounds of the group consisting of ethylene, propane and ethane.

13. The method of claim 10, wherein said supercritical fluid is selected from one or more compounds of the group consisting of nitrous oxide, nitrogen and carbon dioxide.

14. The method according to claim 1, wherein said mammalian soft tissue is derived from an organ.

15. The method according to claim 1, wherein said mammalian soft-tissue is nerve tissue.

16. The method according to claim 1, wherein said mammalian soft-tissue is muscle tissue.

17. The method according to claim 1, wherein said mammalian soft tissue is adipose tissue.

18. The method according to claim 1, wherein said mammalian soft-tissue is glandular tissue.

19. A method according to claim 1, wherein said mammalian soft-tissue is epithelial tissue.

20. The method according to claim 1, wherein said mammalian soft-tissue is endothelial tissue.

21. The method according to claim 1, wherein said mammalian soft tissue is myocardial tissue.

22. The method according to claim 1, wherein said mammalian soft-tissue is vascular tissue.

23. The method according to claim 1, wherein said mammalian soft tissue is lymphatic tissue.

24. The method according to claim 1, wherein said mammalian soft tissue comprises respiratory tissue.

25. The method according to claim 1, wherein said mammalian soft tissue comprises digestive tissue.

26. The method according to claim 1, wherein said mammalian soft tissue comprises sensory tissue.

27. The method according to claim 1, wherein said mammalian soft tissue comprises urinary tissue.

28. The method according to claim 1, wherein said mammalian soft tissue comprises reproductive tissue.

29. The method according to claim 1, wherein said method further comprises adding a modifier or entrainer to said supercritical fluid.

30. The method according to claim 29, wherein said modifier or entrainer is a surfactant.

31. The method as in claim 29, wherein said modifier or entrainer is water.

32. The method according to claim 29, wherein said modifier or entrainer is an alcohol.

33. The method according to claim 32, wherein said alcohol is ethanol.

34. The method according to claim 32, wherein said alcohol is n-propanol.

35. The method according to claim 29, wherein said modifier or entrainer is a ketone.

36. A method as in claim 35, wherein said ketone is acetone.

* * * * *